(12) United States Patent
Hagberg et al.

(10) Patent No.: US 9,315,515 B2
(45) Date of Patent: *Apr. 19, 2016

(54) METHOD OF MAKING INTERNAL DEHYDRATION PRODUCTS OF SUGAR ALCOHOLS

(71) Applicant: ARCHER DANIELS MIDLAND COMPANY, Decatur, IL (US)

(72) Inventors: Erik Hagberg, Decatur, IL (US); Erin M. Rockafellow, Decatur, IL (US); Brennan Smith, Decatur, IL (US); Kenneth F. Stensrud, Decatur, IL (US)

(73) Assignee: Archer Daniels Midland Company, Decatur, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/437,258

(22) PCT Filed: Oct. 4, 2013

(86) PCT No.: PCT/US2013/063356
§ 371 (c)(1),
(2) Date: Apr. 21, 2015

(87) PCT Pub. No.: WO2014/070371
PCT Pub. Date: May 8, 2014

(65) Prior Publication Data
US 2015/0307510 A1    Oct. 29, 2015

Related U.S. Application Data

(60) Provisional application No. 61/720,453, filed on Oct. 31, 2012.

(51) Int. Cl.
*C07D 493/04* (2006.01)
*A61K 31/34* (2006.01)

(52) U.S. Cl.
CPC .............. *C07D 493/04* (2013.01); *A61K 31/34* (2013.01)

(58) Field of Classification Search
CPC ..................................................... C07D 493/04
USPC .......................................................... 549/464
See application file for complete search history.

(56) References Cited

U.S. PATENT DOCUMENTS 9,115,146 B2 *   8/2015   Sanborn ............... C07D 493/04

* cited by examiner

*Primary Examiner* — Golam M M Shameem
(74) *Attorney, Agent, or Firm* — William B. Miller

(57) ABSTRACT

A process is provided for making isohexides such as isosorbide with reduced color and/or improved color stability on storage, wherein ionic species in the crude dehydration product mixture are chromatographically substantially separated from the remainder of the crude product mixture, then the remainder is refined to yield a finished product for further use or sale.

9 Claims, 3 Drawing Sheets

METHOD OF MAKING INTERNAL DEHYDRATION PRODUCTS OF SUGAR ALCOHOLS

FIELD OF THE INVENTION

The present invention relates generally to methods for making an internal dehydration product of a sugar alcohol and to compositions including one or more such materials. The present invention relates also to compositions including these materials which can be described as having reduced color and/or as being color stable on storage under generally prevailing storage conditions, and to the methods for making such reduced color and/or color stable compositions.

BACKGROUND ART

Sugar alcohols derived from six-carbon sugars (otherwise known as hexitols), such as, for example, sorbitol, mannitol, iditol and galactitol, have been long known. Particularly in recent years, significant interest has been expressed in the possible use of the internal dehydration products of such materials to displace petroleum-based materials in a number of commercially important applications. Dianhydrohexitols such as isosorbide, isomannide and isoidide, as made by the acid-catalyzed removal of two water molecules from the original internal structure of the corresponding hexitol, have been used or proposed for use in place of petroleum-based monomers such as terephthalic acid, for instance, though particularly in the case of isosorbide a substantial number of additional uses have been, are being or are envisaged to be developed.

As related in U.S. Pat. No. 7,122,661 and in U.S. Pat. No. 8,008,477, however, it has heretofore generally been required for the majority of these uses to apply a purification treatment to the compositions resulting directly from an acid-catalyzed dehydration step, as these compositions will typically contain each of the stereoisomers isosorbide, isomannide and isoidide, as well as less dehydrated materials such as sorbitan, mannitan and iditan, a variety of oxidation or degradation products, oligomeric and polymeric byproducts and various other "highly coloured species of a poorly defined nature", see, e.g., U.S. Pat. No. 8,008,477 at column 2, line 35.

As summarized in the aforementioned U.S. Pat. No. 7,122,661 and U.S. Pat. No. 8,008,477, a number of approaches had been suggested previously for obtaining the internal dehydration products (and particularly for obtaining the dianhydrohexitols such as isosorbide especially) in greater purity, for a variety of reasons. Some of these approaches sought improvements in purity through changes to the dehydration process by which the dianhydrohexitols are made, while other approaches involved a form of purification after the dianhydrohexitol compositions are formed.

For example, GB 613,444 describes the production of an isosorbide composition through dehydration carried out in a water/xylene medium, followed by distillation and recrystallization from an alcohol/ether mixture.

WO 00/14081 describes distillation and recrystallization from a lower aliphatic alcohol, or distillation alone in the presence of sodium borohydride and in an inert atmosphere.

U.S. Pat. No. 4,408,061 uses gaseous hydrogen halide or liquid hydrogen fluoride dehydration catalysts with carboxylic acid cocatalysts followed by distillation of the crude isosorbide or isomannide compositions thus obtained.

U.S. Pat. No. 4,564,692 briefly mentions prepurification on "ion exchangers and/or activated charcoal", followed, after concentration by evaporation and seeding of crystals of the desired isohexide, by crystallization from water.

Rather than modifying conventional acid-catalyzed dehydration methods or using different, often costly techniques to clean up the direct products of such methods as in the above references, it has also been proposed to generate the dianhydrohexitols by means of certain bimetallic catalysts in the presence of hydrogen. For example, EP 380,402 describes synthesis of the dianhydrohexitols by reacting sugar alcohols with hydrogen under pressure and in the presence of particular catalysts based on a combination of copper and a noble metal or gold.

U.S. Pat. No. 6,013,812 observes, however, that these catalysts tended to lose activity fairly rapidly, and proposes an improvement to a conventional acid-catalyzed dehydration wherein acid-stable Ru, Rh, Pd and/or Pt based hydrogenation catalysts and hydrogen are used during the dehydration step.

U.S. Pat. No. 7,122,661 for its part describes a process for obtaining isohexide compositions of 99.5% or greater purity and improved storage stability, without necessarily involving a comparatively costly and low yielding post-distillation crystallization step from a solvent medium, through using an ion-exchange step followed by a decolorization treatment step. More particularly, a distilled isohexide composition is described as subjected to treatment with at least one ion-exchange means, which can be a mixed bed of anionic resin(s) and cationic resin(s) or a succession of cationic resin(s) and anionic resin(s), followed by treatment with at least one "decolorizing means". The decolorizing means can be activated charcoal in granular or pulverulent form. In certain embodiments, a second treatment with the decolorizing means is contemplated before the ion-exchange treatment step. Improved stability isosorbide compositions were said to be produced by the process, though the same steps—ion-exchange treatment followed by decolorizing means treatment—were surprisingly said to result in a destabilizing effect when performed in the reverse order.

U.S. Pat. No. 8,008,477, assigned to the same owner as the '661 patent and having one of the inventors of the '661 patent as its sole named inventor, describes an alternate process for preparing a stable isosorbide composition. According to the '477 patent, the stability of an isohexide composition is not necessarily correlated with its purity, and preparation in an inert atmosphere and/or in the presence of sodium borohydride in the dehydration or in the distillation step likewise did not materially improve the stability of these compositions, col. 3, lines 58-67. Rather, "only" the use of specific stabilizing agents in nongaseous form and after the distillation step was helpful for improving the storage stability of isohexide compositions at ambient and moderate temperatures, col. 4, lines 1-14. Suitable "stabilizing agents" are chosen from the group comprising reducing agents, antioxidants, oxygen scavengers, light stabilizers, anti-acid agents, metal-deactivating agents and mixtures of at least any two of such materials, col. 4, lines 48-53. In certain embodiments, an optional further "purification step" was taught following the distillation, an example being the use of both ion exchange and decolorizing means of the type described in the earlier '661 patent.

SUMMARY OF THE INVENTION

The following presents a simplified summary of the invention in order to provide a basic understanding of some of its aspects. This summary is not an extensive overview of the invention and is intended neither to identify key or critical elements of the invention nor to delineate its scope. The sole purpose of this summary is to present some concepts of the invention in a simplified form as a prelude to the more detailed description that is presented later.

In one aspect, the present invention relates to a process for making reduced color, stable isohexides wherein, prior to distillation, chromatographic resolution or other methods for working up a dehydration product mixture from the acid-catalyzed dehydration of one or more hexitols to provide the isohexide product from within the dehydration product mixture, ionic species in the dehydration product mixture are first chromatographically substantially separated from the remainder of the dehydration product mixture, then the remainder undergoes one or more of distillation, chromatography, solvent recrystallization, melt crystallization and solvent washing and filtration to yield a product enriched in at least one isohexide compared to the remainder.

In certain embodiments, the residual material following the substantial separation of ionic species from the dehydration product mixture and following the further processing of the remainder of the dehydration product mixture to yield the isohexide-enriched product is recycled to the dehydration step of the manufacturing process.

In still other embodiments, the substantial separation of ionic species from the crude dehydration product mixture is combined with the addition of an antioxidant before the further processing to yield an isohexide-enriched product, with a catalytic hydrogenation step before and/or after the further processing to yield an isohexide-enriched product or with both of these further steps.

DESCRIPTION OF EMBODIMENTS

In a first aspect, as just mentioned, the present invention relates to a process for making reduced color, stable isohexides wherein, prior to distillation, chromatographic resolution or other methods for working up a dehydration product mixture received from the acid-catalyzed dehydration of one or more hexitols in order to provide the isohexide product from within the dehydration product mixture for use or for sale, certain impurities present in the dehydration product mixture are first chromatographically substantially separated from the dehydration product mixture, then the remainder undergoes one or more of distillation, chromatography, solvent recrystallization, melt crystallization and solvent washing and filtration to yield a product enriched in the isohexide compared to the dehydration product mixture.

Whereas the '477 patent indicates that the color stability of an isohexide composition is "not necessarily" related to its purity, we have in fact identified a number of materials which are or may be present in the crude dehydration product mixture and have confirmed that these impurities do relate (directly or indirectly) to the presence or formation of color in a conventional 100 percent molten finished isohexide product or in a conventional 85 weight percent solution product.

For the preparation of isosorbide from sorbitol by acid-catalyzed dehydration, these materials can include organic and inorganic salts, acids (for example, formic acid and levulinic acid), acid esters (e.g., sulfate esters from a sulfuric acid catalyzed dehydration step, phosphate esters from phosphoric acid catalyzed dehydration and in general the acid esters from a given oxygen acid catalyzed dehydration step) and their conjugate bases, furanics (e.g., 2-acetylfuran, 5-methylfurfural and various five carbon furanics), oligomeric and polymeric materials from, e.g., acid-catalyzed condensation of various ether functionalized impurities in a crude isosorbide product.

Figure 3:
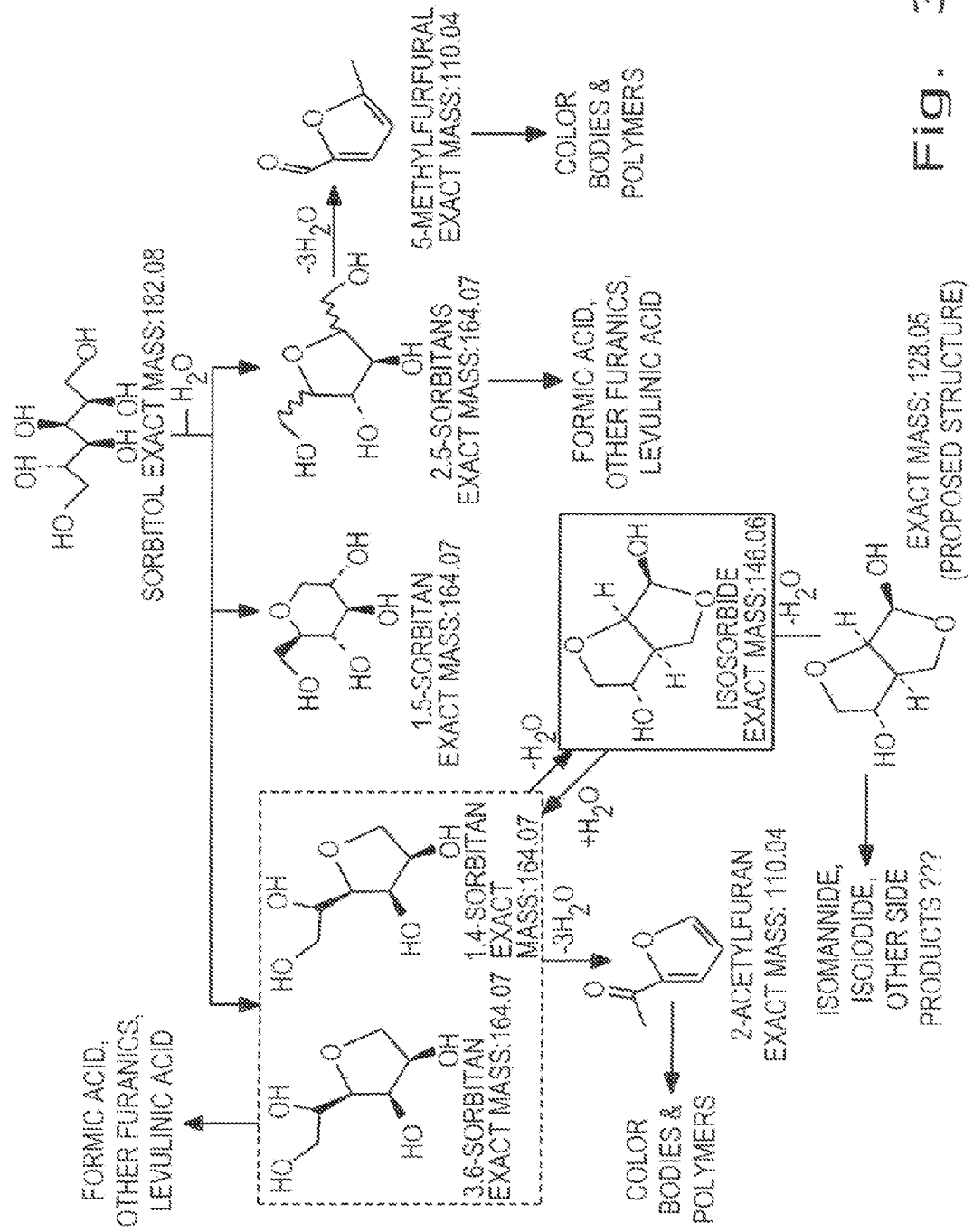
FIG. 3 depicts a proposed dehydration and degradation reaction pathway for a sulfuric acid-catalyzed dehydration of sorbitol, based on information obtained by liquid chromatography/mass spectroscopy, gas chromatography/mass spectroscopy and by ion chromatography of a crude dehydration product.

More particularly, without being bound and without limiting the present invention in any sense, FIG. 3 depicts a number of materials which have been identified or are believed to be present in the crude dehydration product mixture from a sulfuric acid-catalyzed dehydration of a commercially available sorbitol product and postulates the pathways by which these materials may be formed, based on the confirmed presence of compounds of a given molecular weight as indicated by gas chromatography/mass spectroscopy and, as to the specifically identified sulfate esters, by liquid chromatography/mass spectroscopy, as well as based on prior experience with the dehydration of sorbitol.

As will be evident to those skilled in the art on considering the complexity of the illustrated postulated pathways, not all materials present in the crude dehydration product mixture have been identified for FIG. 3 or even attempted to be identified nor quantified, and different (but generally similar) species can be expected in the dehydration of other hexitols by other processes or means than by the use of sulfuric acid. As well, upon distillation (or other further processing) of a crude dehydration product mixture of this character, still other compounds can be expected to form in varying degrees dependent on the particular distillation conditions employed, for example.

Further, while the materials present in a crude dehydration product mixture at a particular point in the overall process of making and finishing an isohexide product and/or some of the compounds formed thereafter in a distillation step, in further processing or even after a certain time in storage may not result in unacceptable color, those skilled in the art will appreciate that ongoing chemical changes that occur in a particular finished isohexide product over a period of time under the storage conditions that can be expected to be experienced by the product, can nevertheless result with the passage of time in the development of unacceptable color in the finished isohexide product.

Despite all of these complexities, we nevertheless consider that certain measures will be effective for producing reduced color and/or improving the color stability of a given finished isohexide product, and expect that those skilled in the art will be well able based on the guidance provided herein and especially based on the working examples below to carry out a chromatographic separation of those impurities and to optionally undertake additional steps as described below, in order to realize a certain reduction in color and/or improvement in color stability on storage of a particular finished isohexide product.

In certain preferred embodiments, the residual material following the substantial separation of the impurities and after the further processing to yield the isohexide-enriched product is of a suitable character to be recycled to the dehydration step of the manufacturing process. Recycle of the distillation bottoms from conventional isosorbide manufacturing (to dehydrate or further dehydrate residual sorbitol or monoanhydrohexitols (sorbitans), respectively, in the bottoms) has previously been impractical because of an offsetting negative effect on conversion in the dehydration step, but as demonstrated below, distillation bottoms from the inventive process can be of a character to be successfully recycled.

As described above, a number of processes have been developed or proposed for making the isohexides/dianhydrohexitols/anhydrosugar alcohols from the corresponding sugar alcohols (and/or monoanhydrosugar alcohols). The manufacture of isosorbide from sorbitol has been particularly of interest. In addition to the processes described in the patents referenced above, commonly-assigned U.S. Pat. No. 6,849, 748; U.S. Pat. No. 7,420,067; and U.S. Pat. No. 7,439,352 are examples of processes that have been developed for making isosorbide from sorbitol, and provide a useful, non-limiting context for describing the present invention.

Accordingly, while understanding that the chromatographic removal step can be incorporated generally in processing a crude dehydration product mixture from the acid-catalyzed dehydration of one or more hexitols according to any of the various previously-known such processes, in one illustrative embodiment, a process as described in U.S. Pat. No. 7,439,352 is modified to at least incorporate chromatographic means for substantially separating ionic species from the crude isosorbide product mixture before the distillation of the remainder as described hereafter.

Figure 1:
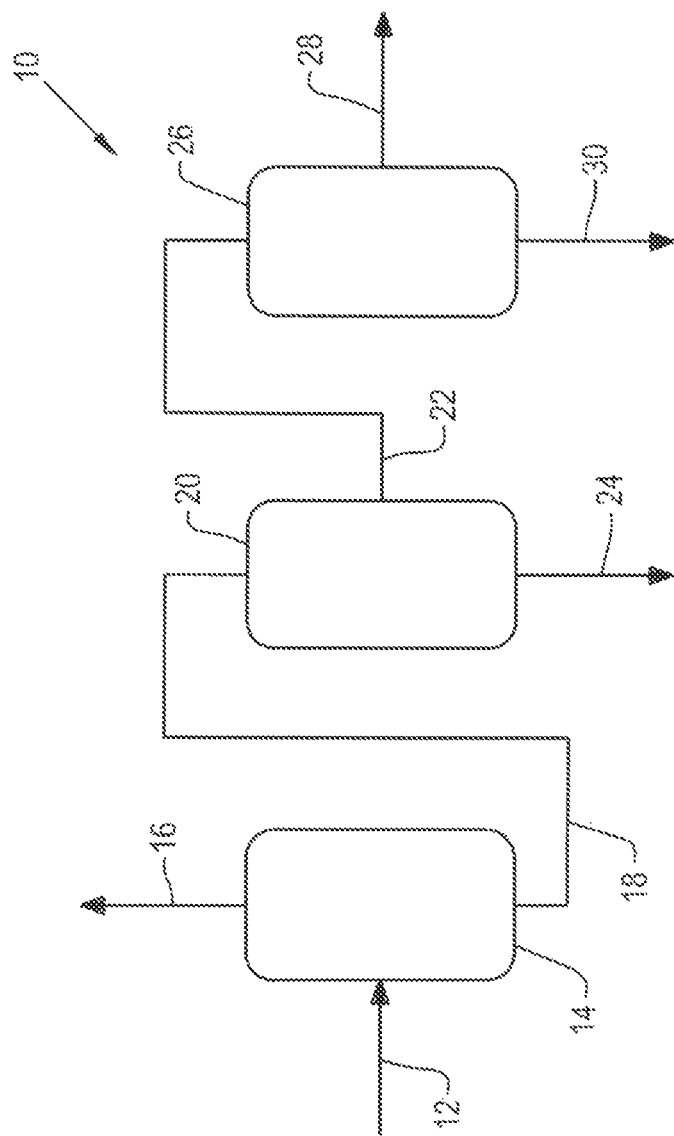
FIG. 1 is a schematic diagram of a process for manufacturing isosorbide from sorbitol in accordance with U.S. Pat. No. 7,439,352.

Turning now to FIG. 1, in a process 10 as originally described in the '352 patent, sorbitol is supplied as indicated by reference numeral 12 to reactor 14. The sorbitol 12 is first heated to a molten state, then is dehydrated in the reactor 14 in the presence of a catalyst for facilitating the dehydration to isosorbide, producing a water effluent 16 and a dehydration product mixture 18 including isosorbide. The dehydration product mixture 18 is then subjected to a first distillation in a first distillation apparatus 20 to form a first isosorbide distillate 22 and a first distillate bottoms 24. The first isosorbide distillate 22 is then subjected to a second distillation in a second distillation apparatus 26 to form a purified isosorbide product 28 and a second distillate bottoms 30.

More particularly, in the first step of the process 10 of FIG. 1, the sorbitol is melted by standard methods that are known in the art. For example, the sorbitol can be melted by placing it in a 3-neck round bottom flask equipped with an agitator, temperature probe, and vacuum line. Preferably, the sorbitol is heated to at least 100 degrees Celsius to 200 degrees Celsius. For sorbitol powder, to provide a specific example, the preferred melting temperature is from 98 degrees Celsius to 105 degrees Celsius, while an even more preferred melting temperature is from 98 degrees Celsius to 100 degrees Celsius. Once molten, the sorbitol is subject to stirring.

A catalyst that will facilitate the dehydration of the sorbitol is then added to the molten starting material. Typically acid catalysts have been used to facilitate the dehydration of sugar alcohols such as sorbitol, including for example soluble acids, acidic ion exchange resins, and inorganic ion exchange materials. Sulfuric acid, phosphoric acid, p-toluenesulfonic acid, and p-methanesulfonic acid are given as examples of preferred soluble acids that may be used, though one of skill in the art would recognize that other soluble acids with similar properties would be useful as well.

Zeolite powders are examples of inorganic ion exchange materials that could be used; specifically an acidic zeolite powder such as a type ZSM-5 ammonium form zeolite powder may be used. Examples of zeolite powders said to be useful include, but are not limited to, CBV 3024 or CBV 5534G (both available from Zeolyst International), and/or T-2665 or T-4480 (both available from United Catalysis, Inc.). One of skill in the art would recognize that other zeolite powders with similar properties may be useful though not specifically listed here.

A sulfonated divinylbenzene/styrene co-polymer acidic ion exchange resin provides an example of a possible acidic ion exchange resin catalyst. Examples include, but are not limited to, AG50W-X12 from BioRad Laboratories, Amberlyst 15 or Amberlyst 35 from Rohm & Haas, RCP21H from Mitsubishi Chemical Corp., and Dowex 50Wx5 (Dow Chemical Co.). The sulfonated divinylbenzene/styrene co-polymer acidic ion exchange resin, Amberlyst 35, is indicated as a particularly preferred resin for the production of isosorbide from sorbitol. One of skill in the art would be aware of other acidic ion exchange resins with similar properties that could be used.

The amount of catalyst used is indicated as generally being on the order of from 0.01 equivalents to 0.15 equivalents by weight. A preferred amount of catalyst is 0.1 equivalents by weight.

The dehydration can be carried out under a vacuum, at elevated temperatures, and with stirring of the reaction mixture. The vacuum can range over a pressure of from 0.05 Torr to 40 Torr, with preferred pressures of from 1 Torr to 10 Torr. As a specific example, a preferred pressure for the dehydration of sorbitol to isosorbide is from 1 Torr to 10 Torr. The temperature for the dehydration can be from 90 deg. C. to 140 deg. C. In certain embodiments, the dehydration temperature can be from 98 deg. C. to 130 deg. C., especially, from 120 degrees Celsius to 130 degrees Celsius. The dehydration can be carried out over a period of approximately 2 hours at such temperatures. The water can be pulled off of the melted sorbitol/catalyst mixture under a vacuum of from 1 Torr to 10 Torr. The dehydration reaction is preferably performed in a reactor which can run in a batch or continuous mode. In embodiments wherein the acid catalyst is a solid acid catalyst (e.g., acidic ion exchange resin), the reactor can preferably hold or contain baskets to which the solid acid catalyst can be added.

Following the dehydration procedure, the resultant dehydration product mixture 18 is purified. In one embodiment, a vacuum distillation is used. In a more specific embodiment, the vacuum distillation is performed using a film evaporator, specifically a wiped film evaporator. One example of a wiped film evaporator apparatus that is useful in the present invention is a vertical agitated thin-film processor. Advantages of using a wiped film evaporator include handling of viscous solutions, improved product purity, and low residence time, which leads to a reduction or elimination of product degradation. Specifically with respect to production of isosorbide from sorbitol, use of a wiped film evaporator was said to provide approximately an 80% yield on distillation, negligible water loss during distillation (which results in reduced polymerization), and to provide for further recovery of isosorbide and sorbitan from the residue. The distillation process results in a first isosorbide distillate 22.

The pot temperature and vacuum used for the first distillation apparatus 20 can vary, but vapor temperatures of from 140 degrees Celsius to 190 degrees Celsius are preferred. More preferred vapor temperatures are from 160 degrees Celsius to 170 degrees Celsius, especially from 165 degrees Celsius to 170 degrees Celsius. The vacuum pressure can be from 0.05 Torr to 40 Torr, preferably being from 1 Torr to 10

Torr. For the vacuum distillation of isosorbide, a vacuum pressure of from 1 Torr to 10 Torr, a pot temperature of 180 degrees Celsius, and a vapor temperature of from 160 degrees Celsius to 170 degrees Celsius are said to be most preferred. Alternative purification methods such as filtration or the addition of activated charcoal with subsequent crystallization are also mentioned as useful.

The first isosorbide distillate 22 is then preferably subjected to a second vacuum distillation in a second distillation apparatus 26, for example, by means of a second wiped film evaporator, providing the purified isosorbide product 28 and the second distillate bottoms 30. The second wiped film evaporator can be of the same type as, or different than, the first wiped film evaporator. The conditions (e.g., vacuum pressure and temperature) of the second vacuum distillation can be the same as, or different than, the conditions of the first vacuum distillation, the parameters of which are described above. The use of two film evaporators allows for production and purification of isosorbide without the use of potentially harmful organic solvents.

In an alternate embodiment described in the '352 patent, the first isosorbide distillate 22 is subjected to melt crystallization wherein the first isosorbide distillate 22 is heated until molten (isosorbide's melting point is about 65 degrees Celsius), and then cooled over time until the crystallization point is reached, but not so much that the material solidifies. In fact, a slurry-like consistency is preferred, so that the material can be centrifuged. As used herein, the term "slurry-like consistency" refers to a material that is a mixture of liquid with several finely divided particles. The centrifugation is performed at a relatively high speed for a relatively short period of time in order to avoid solidification of the material, and also to avoid having the desired isosorbide product drawn off with the impurities. For example, the centrifugation can be performed at 3000 to 4000 rpm for 5 minutes, though those skilled in the art will appreciate that the duration of centrifugation will ideally vary depending on the amount of material to be purified. The resultant isosorbide in any case is indicated as being at least 98% pure, and in most cases being greater than 99% pure (depending upon the solidity of the "slurry").

Alternatively, the '352 patent also contemplates that the first isosorbide distillate 22 can be subjected to solvent recrystallization. Solvents mentioned as useful include, but are not limited to, acetone, ethyl acetate, and low molecular weight alcohols such as ethanol and methanol.

In still another embodiment mentioned in the '352 patent, further purification of the first isosorbide distillate 22 can involve subjecting the first distillate 22 to a solvent wash, followed by filtration. Preferably, the solvents are cold, for example, having a temperature of 0 degrees Celsius to 23 degrees Celsius. Solvents mentioned included acetone, ethyl acetate, and low molecular weight alcohols such as ethanol and methanol. Filtration was described as carried out by means well known in the art.

In one embodiment of a process according to the present invention, a process according to any of the aforementioned embodiments described in U.S. Pat. No. 7,439,352 is modified to include one or both of ion exchange and ion exclusion to remove ionic species before the further purification of the remainder of a crude dehydration product mixture, for example, by successive distillation steps as shown in FIG. 1.

Figure 2:
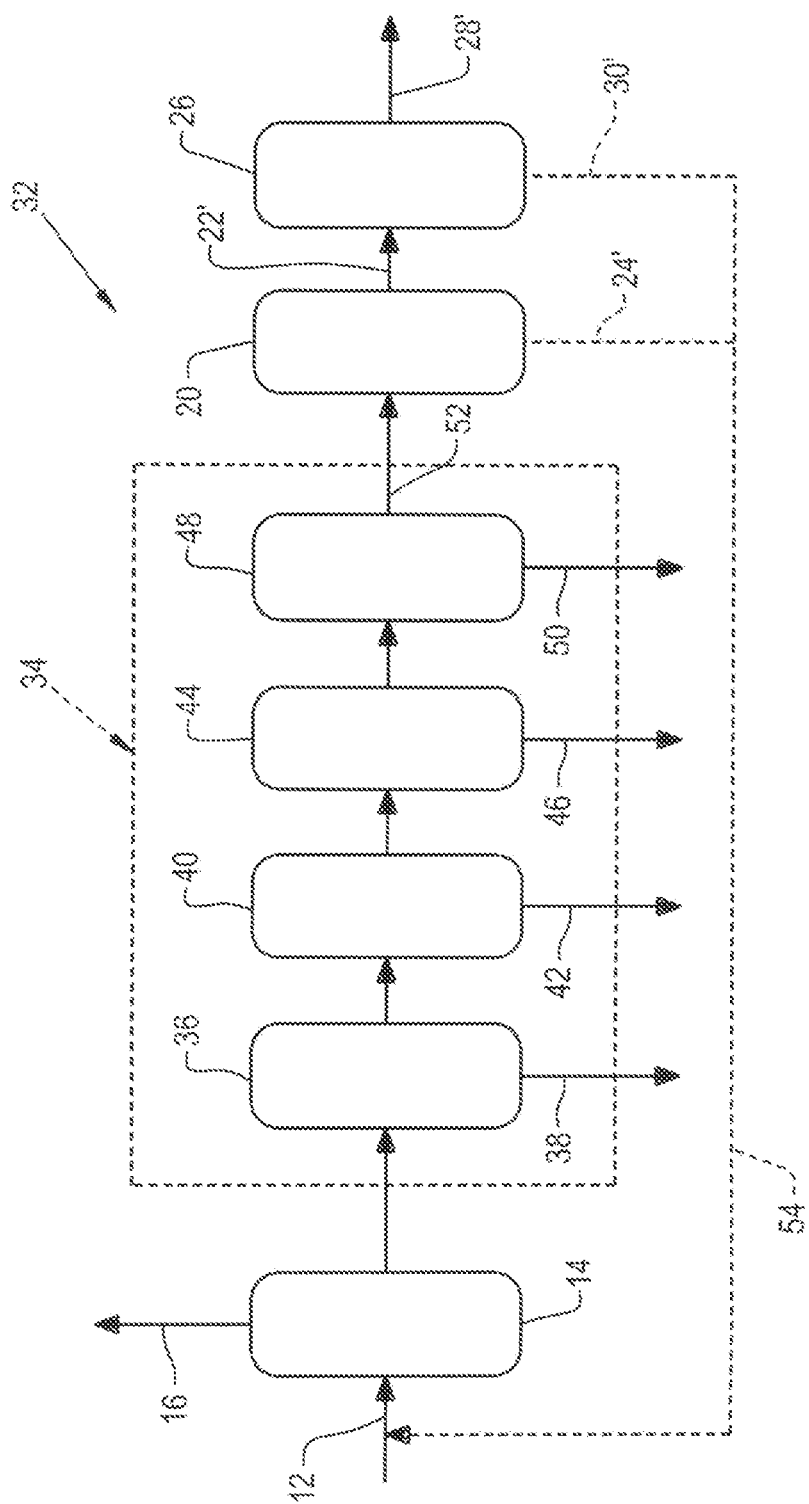
FIG. 2 is a schematic diagram of the process of FIG. 1, modified in accordance with the present invention to include a chromatographic separation of inorganic salts and other ionic materials from a crude dehydration product mixture prior to a refining of the crude dehydration product mixture to provide an isosorbide product for use or sale.

An example of such a modified process 32 is schematically illustrated in FIG. 2, in which a crude isosorbide impurity removal system 34 of the present invention is deployed upstream of the first distillation apparatus 20, with the other elements of the process 32 prior to the system 34 being as previously described in respect of FIG. 1 (as indicated by the use of the same reference numbers). In the particular embodiment of the system 34 depicted in FIG. 2 and further described hereafter, nanofiltration or ultrafiltration, ion exclusion, ion exchange and carbon or resin bed adsorption work together in combination to remove substantially all of the ionic species from the crude dehydration product mixture 18, as well as removing other species (or the precursors of such species) contributing to the development of color in the finished isohexide product, especially on storage. These various ionic and other species may include, as mentioned previously and as suggested by FIG. 3, such materials as solubilized organic and inorganic salts, formic and levulinic acids, formate and levulinate esters, as well as other acid esters (e.g., sulfate esters from a sulfuric acid catalyzed dehydration step, phosphate esters from phosphoric acid catalyzed dehydration and in general the acid esters from a given oxygen acid catalyzed dehydration step) and their conjugate bases, furanics, oligomeric and polymeric materials and related degradation intermediates or precursors.

In quantitative terms, preferably not more than 1000 ppm of total ionic species remain in the crude dehydration product mixture, on an overall weight basis, after the crude isosorbide impurity removal system 34. More preferably, no more than 100 ppm remain, and most preferably no more than 50 ppm remain.

Alternatively, given the numbers of dehydration and degradation products that may be made in the dehydration of sorbitol (as partly demonstrated in FIG. 3), "substantially all" of the color-associated impurities can be considered as having been separated when no more than 100 ppm remains of formic acid, though more preferably no more than 10 ppm of formic acid remains after the crude isosorbide impurity removal system 34 and still more preferably no more than 1 ppm remains.

Returning now to FIG. 2, where both ion exclusion and ion exchange are used, either can be used before the other, with carbon or resin bed adsorption optionally but preferably following in particular to remove nonionic oligomeric and polymeric impurities. Optionally, but also preferably as shown in FIG. 2, nanofiltration or ultrafiltration is used upstream of an ion exclusion step, an ion exchange step or both, primarily to protect the resins from fouling with especially higher molecular weight, oligomeric or polymeric species as may be formed in the crude dehydration product mixture 18, for example, by the proposed reaction pathways shown in FIG. 3.

Molten sorbitol 12 is dehydrated in the reactor 14 using sulfuric acid to produce a crude dehydration product mixture 18. The mixture 18 is typically neutralized with a strong base such as sodium hydroxide, then dilution water is added to a 65 percent solution. The neutralized crude dehydration product mixture 18 is then supplied to the crude isosorbide impurity removal system 34.

The particular crude isosorbide impurity removal system 34 illustrated in FIG. 2 includes a first, nanofiltration or ultrafiltration step 36 to remove at least those higher molecular weight, oligomeric or polymeric impurities in the crude dehydration product mixture 18 (as indicated by retentate 38) that have tended in our experiments to precipitate out and foul subsequent ion exchange and/or ion exclusion resins. For the sulfuric acid-catalyzed crude isosorbide product mixtures used below in our examples, we found that membranes having a molecular weight cut-off of about 1,000 to 10,000 were satisfactory, though those skilled in the art will appreciate that for other crude isohexide product mixtures produced by different methods or under different conditions, other nanofiltration or ultrafiltration membranes may be best or may not be economically worthwhile to implement at all. Examples of the membranes we have tried and found useful under our particular conditions include GE Power and Water GE-series, and PW-series polyethersulfone ultrafiltration membranes, Sepro PES5, PES10 polyethersulfone, and PVDF4 polyvinylidine fluoride ultrafiltration membranes.

Where fouling of subsequent ion exchange and/or ion exclusion resins is a concern, other measures may be considered as well as alternatives to the use of nanofiltration or ultrafiltration membranes. For our purposes, the inclusion of a nanofiltration or ultrafiltration step 36 was effective for preventing the fouling, so that we did not undertake to determine whether the fouling was at least in part a function of cooling of the crude dehydration product mixture 18 that reduced the solubility of the higher molecular weight materials in the mixture 18 (which could be addressed by jacketing, insulating, steam tracing and the like) or at least partly related to the pH of the crude dehydration product mixture 18 (which could be addressed by tighter pH control on neutralization).

Following the nanofiltration or ultrafiltration step 36, an ion exclusion step 40 is employed for removing ionic species (42) from the filtered crude dehydration product mixture 18 through simulated moving bed chromatography using at least one strong acid cation exchange resin. Preferred resins are chromatographic grade, gel type resins with a volume median diameter between 290-317 μm, where more than 80% of the particle size range is between 280-343 μm and more than 60% of the particle size range is between 294-392 μm, which are characterized by a crosslink density of less than 12%, more preferably less than 8% and ideally less than 6%, and which are in the cation form corresponding to the highest concentration cation present in the crude dehydration product mixture 18. The ion exclusion step 40 may be conducted in a batchwise, semibatch or continuous manner and may be conducted through a fixed bed arrangement or a continuous simulated moving bed system.

In the particular embodiment 32, ion exclusion step 40 is followed by an ion exchange step 44 for removing additional ionic impurities (46), through the use of preferably a fixed bed arrangement including at least one highly crosslinked strong acid cation exchange resin in the hydrogen form and one macroporous, highly crosslinked strong base anion exchange resin in the hydroxide form. As with the materials used for the ion exclusion step 40, while particular examples follow hereafter, various resins of the indicated types are commercially available and known to those skilled in the art, and it will be well within the capabilities of those of ordinary skill in the use of such ion exchange resins to select and use appropriate resins effectively in the ion exchange step 44 to remove additional impurities of the types listed above from the crude dehydration product mixture 18.

A carbon or resin bed adsorption step 48 is then used in the embodiment 32 principally to remove further nonionic oligomeric and polymeric impurities and/or color bodies (50) that may remain. Preferably a fixed bed arrangement with one or more activated carbons is used. Suitable activated carbons include but are not limited to Norit® SA2 steam activated carbon from peat, Calgon CPG®-LF low acid soluble iron content granular activated carbon from coal, Calgon CAL® coal-based granular activated carbon. Nuchar® SN chemically activated, wood-based powdered activated carbon, Norit® RO 0.8 high surface area pelletized activated carbon. Nuchar® WV-B low density, high surface area granular activated carbon, Calgon PCB® activated carbon from coconut shells, Calgon BL® powdered, reagglomerated coal-based activated carbon, Nuchar® RGC high activity, tow ash, low soluble iron granular activated carbon, and Nuchar® SA-20 chemically activated, wood-based powdered activated carbon. Suitable adsorptive resins include but are not limited to macroporous styrene-divinylbenzene type resins, for example, Dowex Optipore L493 and Dowex Optipore SD-2 resins.

The remainder 52 of the crude dehydration product mixture 18 following the crude isosorbide impurity removal system 34 is then filtered (not shown) to remove any of the resin(s) and carbon(s) from the system 34 that may be carried over in the remainder 52. The remainder 52 is then further processed to ultimately yield a finished isosorbide product (28' in FIG. 2) which is enriched in the desired isosorbide material compared to the crude dehydration product mixture 18 and which can be used for making additional products or sold. In the particular illustrative embodiment shown schematically in FIG. 2, initially water is removed from the filtered remainder 52 in a dewatering step (not shown) and the remainder 52 is degassed of light gases (not shown). In that color develops more readily in these isohexide products with the development of a heat history in the making and purification of these materials, preferably the dewatering step involves lower temperatures and higher vacuum. Thereafter enrichment in the isosorbide can be conventionally achieved by known refining methods, for example, through successive distillations in first and second distillation apparatus 20 and 26, respectively, with the first and second distillation apparatus 20 and 26 preferably making use of thin or wiped film evaporation as in FIG. 1 to minimize further heat history on the desired isosorbide product 28'.

The removal of impurities via system 34 in advance of distilling a crude isosorbide product has been found to provide significantly higher yields (through the prevention of yield losses to, for example, various degradation products formed in the manner suggested by FIG. 3 or otherwise) with lower intrinsic color and improved color stability as compared to where the system 34 is not used, and a crude isosorbide product containing the impurities is distilled. The removal of the impurities also enables a further yield-enhancing refinement, in that isosorbide distillation bottoms (24' and 30' in the illustrative embodiment of FIG. 2 are combined to provide isosorbide distillation bottoms stream or aggregation 54) from the subsequent distillation step can be recycled to the front of the process so that unconverted sorbitol and sorbitan partial dehydration products can be used to make additional isosorbide. Previously, the isosorbide distillation bottoms have not been amenable to being recycled in this manner, as impurities removed by system 34 have tended to adversely affect the dehydration undertaken in the reactor 14.

In one alternative embodiment that may be considered, the isosorbide distillation bottoms containing some sorbitans can be dehydrated separately and not recycled, under conditions optimized for the dehydration of sorbitans rather than sorbitol. In another alternative embodiment, the isosorbide distillation bottoms may have a sufficiently improved color as to be useful directly in certain less demanding isosorbide product end uses and applications. In yet another alternative embodiment that may be considered, sorbitans are themselves useful products for certain applications (e.g., in food products), so that at least some portion of the sorbitans may be removed for these applications from the isosorbide distillation bottoms before recycling the remainder.

In still other embodiments, the substantial separation of ionic species from the crude dehydration product mixture may be combined with the addition of one or more antioxidant additives before the remainder of the crude dehydration product mixture (52 in FIG. 2) is further processed—through one or more of distillation, chromatography, solvent recrystallization, melt crystallization and solvent washing and filtration—to yield an isohexide-enriched product, consistent with the teachings of our commonly-assigned U.S. Patent Application Ser. No. 61/720,466, filed Oct. 31, 2012 for "ADDITIVES FOR IMPROVED ISOHEXIDE PRODUCTS". Preferred antioxidants have sufficient volatility to at least partially co-distill with the isohexide, and are highly soluble in the isohexide.

Preferred antioxidants for color-stabilizing isosorbide include di-tert-butyl-4-methoxyphenol (or DTMP, CAS 128-37-0), butylated hydroxyanisole (BHA, mix of 2- and 3-tert-butyl-4-hydroxyanisoles, CAS 25013-16-5), 2,6-dimethoxy-4-methylphenol (DMMP, CAS 6638-05-7) and 2,6-dimethoxy-4-methylphenol (DMMP, CAS 91-10-1). Of these, BHA and DMMP are preferred.

The amount of antioxidant(s) employed can range from as little as 10 parts per million by weight of the remainder. In other embodiments, the amount of antioxidant(s) can be from 100 parts per million by weight. In still other embodiments, the amount of antioxidant(s) can be from 300 parts per million by weight of the remainder. Generally the amount added will be just sufficient to provide, in combination with the present invention or with the present invention together with a catalytic hydrogenation procedure to be described hereafter, the improvements in color and in color stability that are needed for a given end use application and for a given isohexide.

In other embodiments, as briefly mentioned above, a process of the present invention—with or without the use of one or more antioxidant additives added subsequent to removing impurities as taught herein but before the remainder of the crude dehydration product mixture is further processed to yield a finished isohexide product—can be combined with a catalytic hydrogenation step conducted before and/or after the further processing to yield an isohexide-enriched product, as further described in greater detail in commonly-assigned U.S. Patent Application Ser. No. 61/720,457, filed Oct. 31, 2012 for "HYDROGENATION OF ISOHEXIDE PRODUCTS FOR IMPROVED COLOR AND/OR COLOR STABILITY".

More particularly, crude dehydration product mixtures and the remainders of crude dehydration product mixtures to which the process of the present invention had been applied may be hydrogenated in the presence of a suitable catalyst, before the crude dehydration product mixture or a remainder of a crude dehydration product mixture is further processed to yield a finished isohexide product for further use or sale. Materials of improved color are produced. Alternatively (or even additionally), an isohexide product following the further processing may be hydrogenated in the presence of a suitable catalyst for improved (reduced) color. Heterogeneous catalysts are preferred, and in combination with the removal of ionic species according to the present invention, hydrogen pressures of less than 6.9 MPa, gauge (1000 psig) and preferably not more than 4.1 MPa, gauge (600 psig) can be effective for providing reduced color products, as further elaborated and demonstrated in the above-referenced, incorporated application.

The color requirements of a given isohexide can vary, of course, from one purchaser to another and from one end use to another. As well, the composition and other attributes (e.g., pH) of the crude dehydration product mixtures themselves can vary according to the methods by which such mixtures have been produced, so that in some instances it may be sufficient to apply a particular solution offered by the present invention or by a commonly-assigned, incorporated reference alone—while in other circumstances it may be necessary to further employ either or both of the measures described in the commonly-assigned, incorporated references. In any event, it is considered that one skilled in the art will be well able to determine the technology or combination of technologies needed to accomplish a needed reduction in color and/or improvement in color stability for a given isohexide product and end use.

While particular color requirements may vary as just mentioned, in general, it is expected that finished 100% molten isohexide products made at least in part by means of the present invention will demonstrate an APHA color as determined in accordance with ASTM D1209 of 100 or less, preferably 20 or less, more preferably 15 or less, and especially 10 or less. In a conventional 85% solution product form, finished isohexide products will preferably demonstrate an APHA color of 100 or less, preferably 20 or less, more preferably 15 or less and especially 10 or less. Preferably, the color stability of these compositions will be such that, after accelerated aging at 85 degrees Celsius for four weeks in the manner of the examples of the incorporated application related to the antioxidant additives, the APHA color of a 100% molten product will still be less than 200. Correspondingly, for an 85% solution product, preferably the APHA color will still be less than 250. Compositions meeting at least the 200 and 250 APHA color criteria for a 100% molten product and an 85% solution product, respectively, will be considered as "color stable" as that term is used herein.

The present invention is further illustrated by the following examples:

EXAMPLE 1

To generate the crude isosorbide product needing to be treated as described herein, granular crystalline sorbitol (3660.0 g, 20.091 mol) was in one instance weighed into a 5 liter, three neck round bottom flask. The flask, fitted with a thermocouple, mechanical stirrer and condenser, was heated to an internal temperature of 140 degrees Celsius using a temperature controlled heating mantel until the sorbitol was molten. Vacuum to <10 Torr was applied through a 1 liter receiver in a dry ice isopropanol bath. Concentrated sulfuric acid (20.3 g, 0.202 mol) was added through a rubber septum using a glass syringe. The reaction was run with mechanical stirring under vacuum (8.9 Torr) at 139.2 deg C. for 100 minutes. The heat was lowered and the temperature reduced to 90.3 deg C. Sodium hydroxide as a 50% solution in water (32.07 g, 0.401 mol) was then added through the septum using a syringe and allowed to stir for at least fifteen minutes. The vacuum was broken and a sample was taken for analysis by GC/FID. Analysis of the resulting crude reaction mixture showed a 99.93% conversion of the sorbitol, a 70.75% mol selectivity to isosorbide and 56.72% weight yield of isosorbide relative to sorbitol. The reaction mixture was then diluted with 1.5 liters of deionized water and filtered through a 0.2 µm filter using a Buchner funnel.

Additional isosorbide was prepared in substantially the same manner in two additional batches, to provide a composited material for the ion exclusion, ion exchange and distillation studies detailed in the following examples. Details of the three batch preparations are found in Table 1 as follows:

TABLE 1

| Rxn Time (min) | Rxn Temp (avg) | Rxn vacuum (avg) | NaOH Added Temp (deg C.) | Acid (wt pct) | NaOH/ H2SO4 (mol) | Rxn water/ sorbitol (mol/mol) | Scale (g) | Conversion | Isosorbide Yield (wt pct) |
|---|---|---|---|---|---|---|---|---|---|
| 87  | 139 | 8.4 | 86.7 | 0.53 | 2.02 | 2.81 | 2000 | 99.9 | 49.8 |
| 90  | 128 | 6.8 | 91.1 | 0.55 | 2.01 | 2.15 | 3600 | 99.4 | 56.6 |
| 100 | 146 | 8.9 | 90.3 | 0.55 | 1.99 | 2.09 | 3600 | 99.9 | 56.7 |

EXAMPLE 2

Separation of Ionic from Non-Ionic Components Using Fixed Bed Ion Exchange Chromatography In a slurry of deionized water, strongly acidic cation exchange resin (DOWEX™ 88 sulfonate functionalized macroporous styrene divinylbenzene strong acid cation exchange resin. The Dow Chemical Company, Midland, Mich.) in the proton form was added to a #25 Ace Glass jacketed chromatography column (25 mm ID×600 mm L) to the 300 cc mark. In a second slurry of deionized water, a strongly basic anion exchange resin (AMBERLITE™ FPA91 CI food grade, macroreticular strong base anion exchange resin, The Dow Chemical Company, Midland, Mich.) in the hydroxide form was added to a #25 Ace glass jacketed chromatography column (25 mm ID×600 mm L) to the 300 cc mark. In a third slurry of deionized water, activated carbon was added to a #25 Ace glass jacketed chromatography column (25 mm ID×600 mm L) to the 300 cc mark. The columns were capped with Teflon adapters and connected in series: 1) cation, 2) anion and 3) carbon, using ⅛" Teflon tubing and Swagelok fittings.

Neutralized isosorbide crude reaction mixture with a composition of approximately 31% by wt isosorbide, 44% by wt sorbitan, 1.7% by wt. sodium sulfate, diluted in deionized water was pumped through the columns using a peristaltic pump at a flow rate of 20 mL/min, at room temperature. The effluent from the columns was dewatered using a rotary evaporator. Analysis by ICP measured 6.2 ppm of residual sodium and 2.4 ppm of residual sulfur (LOD: 0.1 ppm). HPLC/UV analysis of the dewatered ion exchanged crude showed non-detectable carboxylic acids. The final product qualitatively showed significant color reduction, from a dark brown starting material to a very light yellow final material.

EXAMPLE 3

Separation of Ionic from Non-Ionic Components Using Simulated Moving Bed Ion Exclusion Chromatography In a simulated moving bed chromatography system (SMB) from Calgon Carbon Corp, Pittsburgh, Pa., twelve #11 Ace Glass chromatography columns (11 mm ID×450 mm L) mounted on a PLC controlled carousel were slurry-packed with a strong acid cation exchange resin (DOWEX™ MONOSPHERE™ 99/310 sulfonate functionalized, styrene divinylbenzene strong acid cation exchange resin) in the sodium form. The columns were capped with Teflon fittings and plumbed with 1/16" Teflon tubing into 4 zones. Liquids were distributed through the system using four Eldex positive displacement pumps.

Isosorbide crude reaction mixture neutralized, diluted with deionized water and filtered through a 0.2 μm filter was analyzed by GC/FID and Karl Fischer to have 46.025 wt. pct. of isosorbide, 7.352 wt. pct. of sorbitans, and 34.940 wt. pct. of water. Analysis by IC and ICP of the feed solution showed 1541 ppm formate, 697 ppm sulfate and 1929 ppm sodium.

The isosorbide solution was fed into column six in zone three at a rate of 1.5 mL/min. Deionized water was used as the eluent and fed into column one in zone one at a rate of 3.08 mL/min. Extract composed of 34.81 wt. pct. of isosorbide, 4.513 wt. pct. sorbitan, 179 ppm formate, 122 ppm sulfate, 217 ppm sodium and 54.67 weight percent of water. Water was taken from column two in zone one at a rate of 4.51 mL/min and returned, as enrichment, into column three in zone two at a rate of 1.73 mL/min resulting in a net product flow rate of 2.78 mL/min. Raffinate composed of 1.748 wt. pct. of isosorbide, 1.659 wt. pct. of sorbitan, 1152 ppm formate, 480 ppm sulfate, 1812 ppm sodium and 86.45 wt pct. of water, was removed from column ten in zone three at a rate of 3.23 mL/min and returned into column eleven in zone four at a rate of 1.43 mL/min resulting in a net raffinate flow rate of 1.8 mL/min.

Countercurrent rotation of the SMB column carousel occurred stepwise at 10.75 minute intervals. The entire system revolved 7.3 times during the course of the 15.6 hr experiment. Based on GC/FID analysis of the samples taken from the extract and raffinate streams, the yield of isosorbide from the separation was 96.9 wt. pct. with a normalized purity increase from 86 percent to 88 percent due to loss of sorbitans into the raffinate. Total ion exclusion of the formate, sulfate and sodium was 80.6 percent by weight, 71.7 percent by weight and 84.4 percent by weight, respectively. Surprisingly, it was observed that the bulk of the color bodies from the feed eluted in the raffinate, resulting in a significantly improved color of the isosorbide solution from dark black, non-transparent feed to a light yellow, completely transparent extract.

EXAMPLE 4

Separation of Ionic from Non-Ionic Components Using Combined Simulated Moving Bed Ion Exclusion and Ion Exchange Chromatography Extracts from a series of simulated moving bed ion exclusion runs conducted substantially as described in Example 3 were combined, yielding about 5 gallons of light yellow isosorbide solution in water having a composition of 29.45 percent by weight of isosorbide, 3.31 weight percent of sorbitans, 133 ppm of formate, 270 ppm of sulfate, 193 ppm of sodium, and 67.14 percent by weight of water. DOWEX™ 88 sulfonate functionalized macroporous styrene divinylbenzene strong acid cation exchange resin in the proton form was slurried with deionized water and added to a 5 liter fixed-bed ion exchange column to the 4 liter mark. DOWEX™ 22 strong base anion exchange resin in the hydroxide form was slurried with deionized water and added to a 5 liter fixed-bed ion exchange column to the 4 liter mark. The ion-excluded isosorbide solution was pumped through the fixed-bed cation and anion exchange columns in series using a peristaltic pump at a flow rate of approximately 40 mL/min. The effluent from the columns was collected, dewatered using a rotovap, and analyzed. The composition of the combined ion-excluded, ion-exchanged isosorbide mixture was 72.20 wt percent isosorbide, 8.12 wt percent sorbitans, 0.8 ppm formate, non-detectable ppm of sulfate, 38 ppm of sodium, 5.63 wt percent of water.

EXAMPLE 5

Distillation of the Ion Excluded, Ion Exchanged Crude Isosorbide Reaction Mixture by Thin Film Evaporator (TFE), with Antioxidant Addition Approximately 3078.86 g of the ion-excluded, ion-exchanged, rotovapped isosorbide solution from Example 4 was added to a five liter, three neck round bottom flask fitted with a thermocouple, magnetic stir bar and condenser. The solution was heated to 110 deg C. using a temperature controlled heating mantel and vacuum was applied through the condenser to 5 Torr. The residual 5.63 wt pct. of water was evaporated from the solution and the vacuum was broken. 2,6-Di-tert-butyl-4-methoxyphenol (1.9415 g, Sigma Aldrich 97%) was added to the hot stirring isosorbide solution under nitrogen and allowed to dissolve. The reaction mixture was cooled to room temperature, bottled and shipped to Pope Scientific, Inc. in Saukville, Wis. for distillation.

The ion-excluded, ion-exchanged and antioxidant-treated crude isosorbide reaction mixture was initially passed through a degasser, configured with an external condenser, to remove residual water, low-boiling compounds, and dissolved gases prior to distillation on the thin film evaporator. The temperature for the degassing was held at 120 degrees Celsius, the condenser temperature was maintained at 35 deg C. and vacuum was set at 15 mm Hg. The isosorbide was fed at 1021 grams/hr, resulting in 1.5 grains of distillate and 1105.0 grams of residue collected.

Degassed isosorbide residue having a composition of 83.81 percent by weight of isosorbide, 0.19 percent by weight of isomannide, 0.07 percent by weight of isoidide, 12.22 percent by weight of sorbitans, and 600 ppm DTMP was then fed into a 2" thin film evaporator (TFE) configured with an internal condenser, at a flow rate of 711 grams/hr. The skin temperature of the main TFE housing was kept at 170 degrees Celsius. Vacuum was held at approximately 1.2 mm Hg. The internal condenser was kept at 75 degrees Celsius. Distillate (135 grams) and residue (31.0 grams) from the TFE were collected and analyzed by GC/FID and by LC/UV/RID. The composition of the isosorbide distillate was 99.53 percent by weight of isosorbide, 0.17 percent by weight of isomannide, 0.08 percent by weight of isoidide, 0.20 percent by weight of sorbitans, and 197 ppm of DTMP. The neat isosorbide distillate color measured 6 on an APHA color scale. The composition of the isosorbide residue was 13.09 percent by weight of isosorbide, 0.00 percent by weight of isomannide, 0.10 percent by weight of isoidide, and 64.51 percent by weight of sorbitans. The mass yield of the distillation based on analysis of distillate and residue samples was 97.1 percent.

A series of additional 2" TFE distillations of the same isosorbide degassed feed described above were completed in which all conditions were held nearly constant and evaporator temperature was increased incrementally. Results of the distillation experiments can be seen in Table 3. Yields of the TFE distillates from reaction mixtures having the ionic content reduced to nondetectable or near non-detectable levels prior to distillation were significantly higher, and color was significantly lower than historical values in which the ionic species were not first removed.

TABLE 3

|  | Sample #1 | Sample #2 | Sample #3 | Sample #4 | Sample #5 | Sample #6 |
| --- | --- | --- | --- | --- | --- | --- |
| Pass 2 (Product Distillation) | | | | | | |
| Evaporator Temperature, ° C. | 150.0 | 155.0 | 160.0 | 165.0 | 170.0 | 175.0 |
| Condenser Temperature, ° C. | 75.0 | 75.0 | 75.0 | 75.0 | 75.0 | 75.0 |
| Vacuum, mm Hg | 1.250 | 1.250 | 1.250 | 1.200 | 1.200 | 1.200 |
| Feed Rate, g/hr | 714 | 788 | 739 | 762 | 711 | 665 |
| Sampling Time, Minutes | 19 | 16 | 19 | 10 | 14 | 12 |
| Total, g | 226.0 | 210.0 | 234.0 | 127.0 | 166.0 | 133.0 |
| Distillate, g | 138.0 | 127.0 | 138.0 | 98.0 | 135.0 | 113.0 |
| Residue, g | 88.0 | 83.0 | 96.0 | 29.0 | 31.0 | 20.0 |
| Distillate Analysis | | | | | | |
| Color (APHA) | 5 | 5 | 6 | 6 | 6 | 6 |
| DTMP (ppm) | 375 | 278 | 240 | 222 | 197 | 159 |
| isosorbide | 99.64% | 99.70% | 99.72% | 99.62% | 99.53% | 99.28% |
| isomannide | 0.23% | 0.20% | 0.19% | 0.17% | 0.17% | 0.15% |
| isoidide | 0.00% | 0.00% | 0.00% | 0.06% | 0.08% | 0.08% |
| total sorbitans | 0.10% | 0.08% | 0.06% | 0.12% | 0.20% | 0.47% |
| Residue Analysis | | | | | | |
| isosorbide | 61.34% | 59.87% | 60.23% | 28.27% | 13.09% | 9.60% |
| isomannide | 0.00% | 0.00% | 0.00% | 0.00% | 0.00% | 0.00% |
| isoidide | 0.11% | 0.11% | 0.12% | 0.12% | 0.10% | 0.08% |
| total sorbitans | 27.86% | 29.55% | 30.67% | 56.69% | 64.51% | 67.05% |
| isosorbide mass yield (%) | 71.8% | 71.8% | 70.4% | 92.3% | 97.1% | 98.3% |

EXAMPLE 6

Distillation of the Ion Exchanged Isosorbide Crude Reaction Mixture by Thin Film Evaporator (TFE) with Recycle of TFE Bottoms Containing No Salts A crude isosorbide product mixture which had been neutralized, diluted, filtered and treated with a series of fixed bed ion exchange resins to remove ionic compounds to non-detectable levels, was then dewatered using a rotary evaporator. The dewatered feed, containing approximately 31.9 percent by weight of isosorbide and 51.9 percent by weight of sorbitans, was then distilled using a 2" POPE thin film evaporator (TFE) having an internal condenser. The feed was added drop-wise at approximately 0.61 grams/min using a glass, pressure equalized addition funnel equipped with a needle valve. The feed was kept at approximately 70 degrees Celsius using heat tape and insulation. The skin temperature of the main TFE housing was kept at 160 degrees Celsius. Vacuum was held at approximately 4.5 Torr using a vacuum controller applied through an external cold trap filled with dry ice and isopropanol to collect volatiles (e.g. residual water). The internal condenser was kept at 82 deg C. using a recirculating bath filled with propylene glycol/water. Spring-loaded Teflon blades rotating at 504 RPM produced a thin film on the inner wall.

Distillate (40.9 g) and residue (84.76 g) from the TFE were collected and analyzed by GC/FID at 89.4 percent and 0.88 percent by weight of isosorbide, respectively, putting the mass yield of isosorbide for this distillation at 98.0 percent by weight.

The still bottoms (84.76 g) were collected and analyzed using GC/FID at 81.1 percent by weight of sorbitans and 0.18 percent by weight of sorbitol. A fraction of the still bottoms (22.9 g) enriched in 1,4-sorbitan was combined with granular crystalline sorbitol (20.0 g, 0.110 mol) in a 2 neck, 100 mL round bottom flask which had been fitted with a rubber septum, short path condenser and magnetic stirring. The mixture was stirred and heated under vacuum until homogeneous, then dehydrated with concentrated sulfuric acid (0.223 g, 0.002 mol) at 140 degrees Celsius and 1 Torr over a period of approximately 180 minutes. The result was a 99.9 percent conversion of the sorbitol, an 89.3 percent conversion of the 1,4-sorbitan, and a 75.1 percent mol selectivity to isosorbide. Historically, distillate bottoms from crude reaction feeds containing ionic species recycled into fresh isosorbide reactions have failed to achieve total conversions above 50%.

The invention claimed is:

1. A process for making an isohexide, comprising:
dehydrating a hexitol in the presence of an acid catalyst to form a crude dehydration product mixture including an isohexide from the hexitol;
chromatographically substantially separating ionic species from the crude dehydration product mixture; then
subjecting the remainder to further processing to yield a product enriched in the isohexide compared to the remainder.

2. A process according to claim 1, wherein a residual following the dehydration, chromatographic separation and further processing steps, containing unconverted hexitol, one or more monodehydrated materials from the hexitol or both unconverted and monodehydrated materials is recycled to the dehydrating step.

3. A process according to claim 1, further comprising adding at least one antioxidant to the remainder before the further processing.

4. A process according to either claim 1 or claim 3, further comprising hydrogenating one or both of the remainder of the crude dehydration product mixture and the product enriched in the isohexide with a source of hydrogen in the presence of a catalyst.

5. A process according to claim 1, wherein ionic species are separated at least in part by ion exclusion chromatography with at least one strong acid cation exchange resin in the cation form corresponding to the highest concentration cation among ionic species in the dehydration product mixture.

6. A process according to claim 1, wherein ionic species are separated at least in part by ion exchange chromatography with a combination of at least one highly crosslinked strong acid cation exchange resin and at least one highly crosslinked strong base anion exchange resin.

7. A process according to claim 1, further comprising contacting the remainder with at least one adsorbent.

8. A process according to claim 7, wherein the at least one adsorbent includes an activated carbon adsorbent.

9. A process according to claim 1, wherein the crude dehydration product mixture passes through at least one nanofiltration or ultrafiltration membrane before being chromatographically processed.

* * * * *